United States Patent [19]

Wood

[11] 4,190,044

[45] Feb. 26, 1980

[54] TELESCOPING INTERMEDULLARY PIN

[76] Inventor: Eugene W. Wood, P. O. Box 672, Magnolia, Ark. 71753

[21] Appl. No.: 933,990

[22] Filed: Aug. 16, 1978

[51] Int. Cl.$^2$ .................. A61F 5/04; A61B 17/18
[52] U.S. Cl. ................................................ 128/92 BC
[58] Field of Search .......... 128/92 BC, 92 B, 92 BA, 128/92 R, 92 G

[56] References Cited

U.S. PATENT DOCUMENTS

| 2,672,861 | 3/1954 | Jonas et al. ................ | 128/92 BC |
| 2,985,168 | 5/1961 | Jonas et al. ................ | 128/92 R X |
| 4,016,874 | 4/1977 | Maffei et al. ............... | 128/92 BC |

FOREIGN PATENT DOCUMENTS 741970  11/1943  Fed. Rep. of Germany ...... 128/92 BC

*Primary Examiner*—Ronald L. Frinks
*Attorney, Agent, or Firm*—Clarence A. O'Brien; Harvey B. Jacobson

[57] ABSTRACT

The device provides the surgeon with an intermedullary pin for the repair of bone fractures. The pin has a main body or base which is inserted in a drilled out marrow cavity of one-half of the broken bone. A portion of the marrow of the cooperating half of the broken bone is drilled out also to accept the telescoping plunger which is positioned in the base. The two halves of the bone are brought together and the telescopic plunger is forced from the base into the drilled out marrow cavity by a stainless steel wire which is connected to the bottom of the telescoping pin and extends out of the bone cavity through the fracture. When the plunger is extended to its desired length, the stainless steel wire is cut and removed from the bone. The telescoping plunger is held against return to the interior of the base by a series of ridges spaced longitudinally along the body of the plunger which cooperate with faces of the resilient side walls of the base which prevent the reinsertion of the plunger into the base by providing an obstacle against which the ridges abut when return force is applied to the plunger.

9 Claims, 16 Drawing Figures

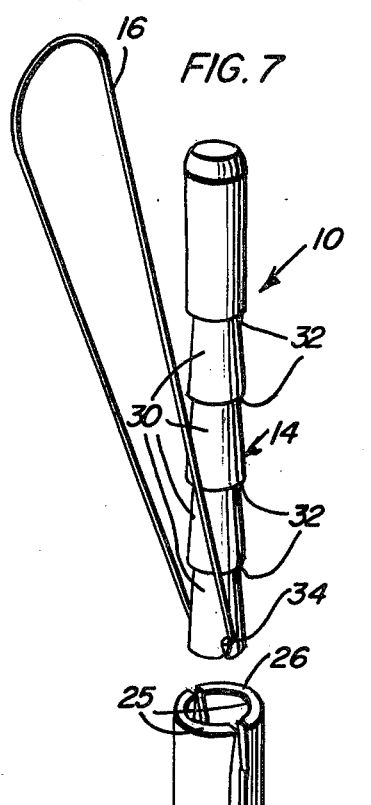
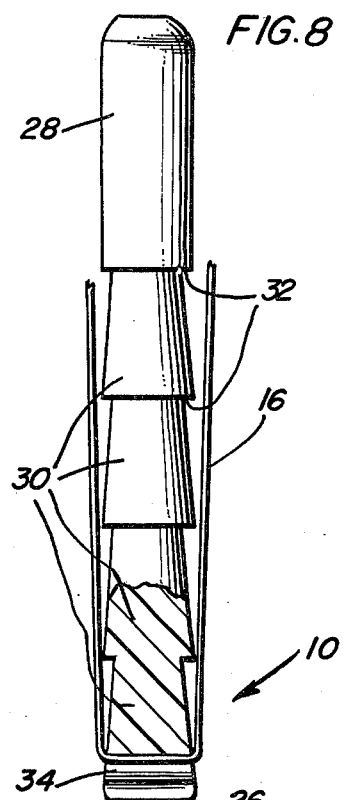
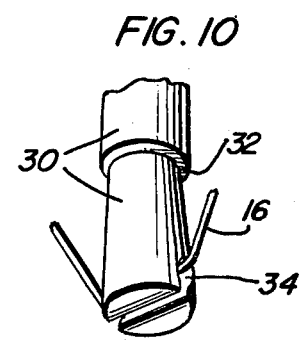
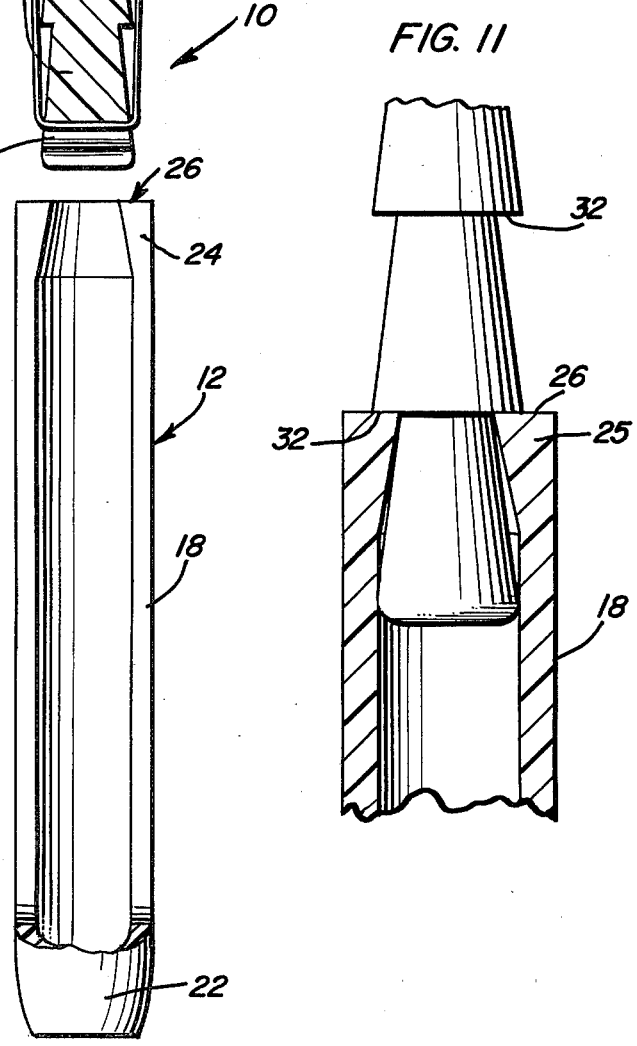
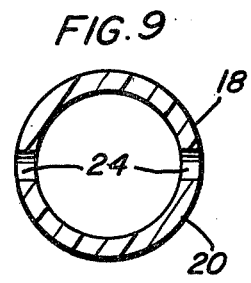

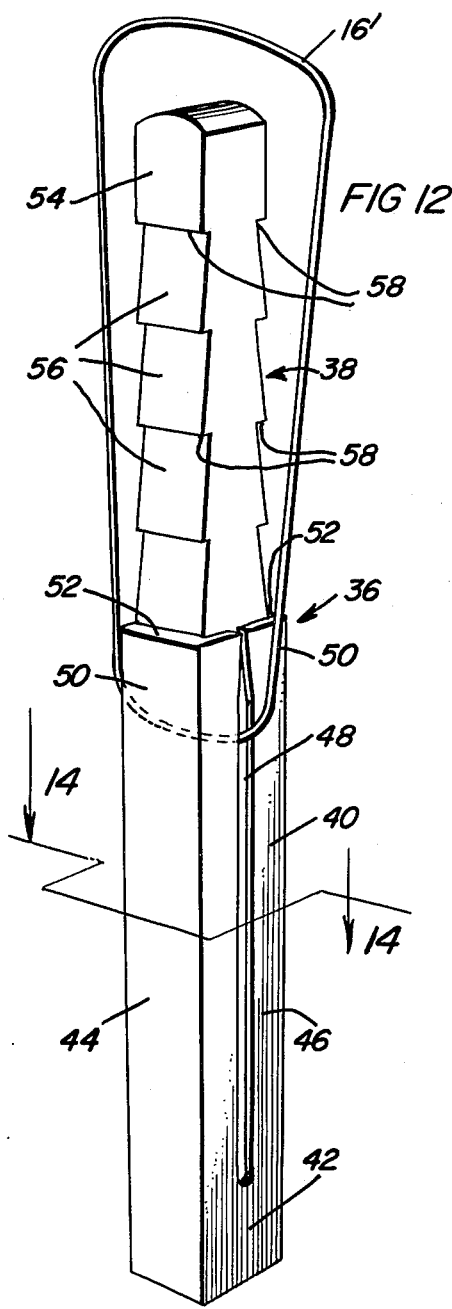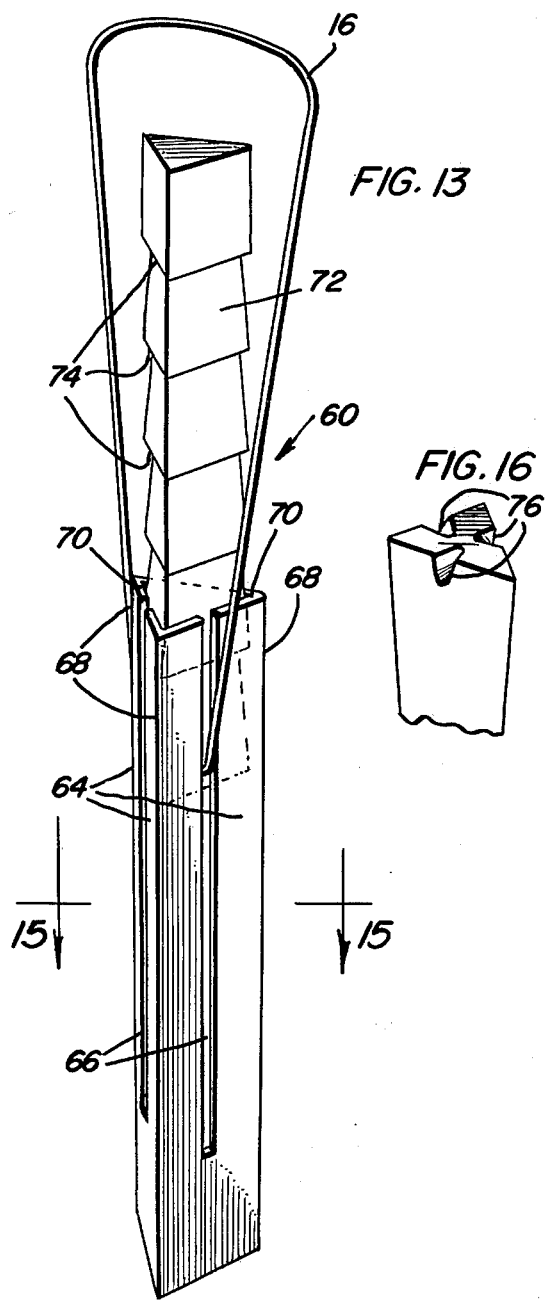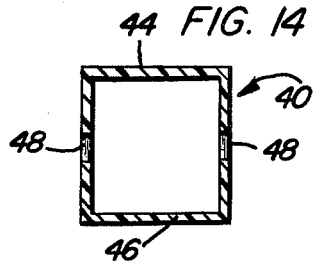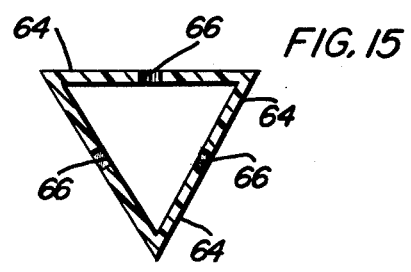

TELESCOPING INTERMEDULLARY PIN

BACKGROUND OF THE INVENTION

1. Field of the Invention

The present invention relates to pins which may be inserted in a medullary cavity by a surgeon to increase the strength of a bone while healing and provide additional strength to the bone after it has healed.

2. Description of the Prior Art

Various intermedullary pins have been used in the past by surgeons to enhance the strength of a fractured bone both during the healing process and after the completion of the healing process. Among these well-known pins the solid non-expanding pin, examples of which may be found in U.S. Pat. No. 2,675,801, issued Apr. 20, 1964, to Bambara, which discloses a solid intermedullary pin comprising a rod shaped member having a substantially cruciform cross section. U.S. Pat. No. 2,998,007, issued Aug. 29, 1961, to Herzog shows an internal tubular splint which extends through the fractured bone and has longitudinal slots through its center. The splint itself is solid except for the slots, and pins are provided for insertion into the slots for holding the splint in place in the bone itself. U.S. Pat. No. 3,717,146, issued Feb. 20, 1973, to Halloran, shows a solid intramedullary pin with threaded ends for engagement with the separated bone halves to secure the pin to the bone for compression stabilization.

Expanding pins for use in the medullary cavity of a fractured bone have also been conceived in the prior art. For example, U.S. Pat. No. 2,672,861, issued Mar. 23, 1954, to Jonas et al, shows an intermedullary pin having a base and a telescoping pin portion wherein the pin is forced from the base by a spring member which is contained within the base. This device has certain inherent disadvantages including the fact that the constant pressure created by the spring has been believed to cause pressure necrosis within the medullary cavity. U.S. Pat. No. 4,016,874, issued Apr. 12, 1977, to Maffei et al, discloses a three-part bone-setting spline pin. The device has two tubular outer members which are screwed into the two halves of the fractured bone. The third member comprises a rod which is inserted into each of the outer members to hold them in proper alignment.

SUMMARY OF THE INVENTION

My intermedullary pin provides a device which aids the surgeon in reducing a bone fracture in short bones and also in long bones which do not lend themselves to conventional pinning without destroying the joint surface either above or below the fracture. My pin may be allowed to remain in the bone after the fracture has healed without fear of any detrimental effects due to its presence within the medullary cavity.

An object of my invention is to provide an intermedullary pin which can easily be expanded within the drilled out marrow cavity of a factured bone and left in its extended position without fear of producing unnecessary pressure upon the surrounding area of the bone.

A further object of my invention is to provide a means for extending the intermedullary pin which means may be easily removed after the pin is extended to its desired length without interferring with the positioning or placement of the extended pin within the cavity. Also, by allowing for the complete removal of my extending mechanism, the mechanism may be made out of materials which, if left within the bone, could hinder the healing process or cause detrimental effects after the bone has healed.

Further, my invention has as an object a pin designed so that it may be made of surgical stainless or other non-tissue responsive materials, such as Teflon, nylon, etc. In this manner, the pin may be left within the bone indefinitely without fear of causing electropoesis, or similar problems caused by the use of metal springs for the extension of telescoping pins.

Yet a still further object of my invention is to provide a telescoping pin which will not re-insert itself into the base portion. My pin provides a beveled top seat to interact with edges provided along the telescoping plunger to insure that the telescoping in may not be forced to reenter the hollow base.

Yet a still further object of my present invention is to provide an intermedullary pin which has a hollowed out base portion with slots along each side to allow marrow to fill the spaces provided in the base and nutrient vessels to feed through the slotted sides.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 7 is an exploded view of the intermedullary pin.

FIG. 8 is an elevational sectional view of the pin showing the connection between the telescoping plunger and the expansion wire.

FIG. 9 is a sectional view taken substantially along a plane passing through section line 9—9 of FIG. 7.

FIG. 10 is a perspective view of the base of the telescoping plunger.

FIG. 11 is an elevational fragmentary view of the interconnection between the telescoping pin and the base.

FIG. 12 is a perspective view showing the square embodiment of the intermedullary pin.

FIG. 13 is a perspective view showing the triangular embodiment of the intermedullary pin.

FIG. 14 is a sectional view taken substantially along a plane passing through section line 14—14 of FIG. 12.

FIG. 15 is a sectional view taken substantially along a plane passing through section line 15—15 of FIG. 13.

FIG. 16 is a perspective view of the bottom of the telescoping plunger of the triangular embodiment of the intermedullary pin.

DESCRIPTION OF THE PREFERRED EMBODIMENTS

Figure 1:
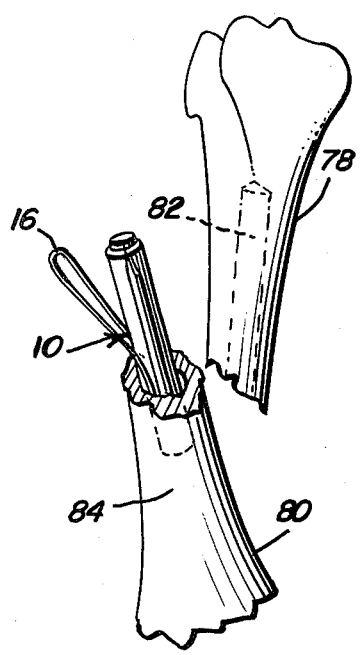
FIG. 1 is a perspective view of the intermedullary pin partially inserted in one-half of a fractured bone.
Figure 2:
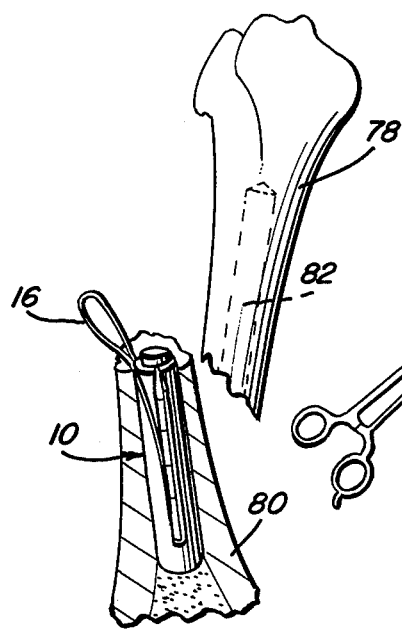
FIG. 2 is a part sectional view of the intermedullary pin inserted into one-half of the fractured bone.
Figure 3:
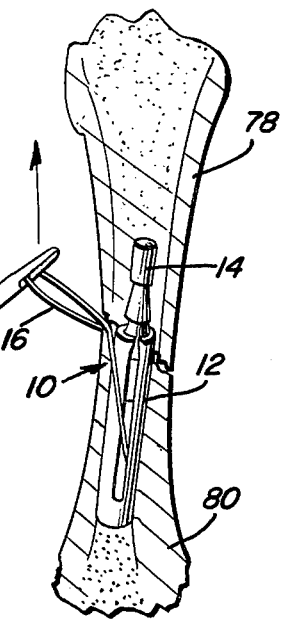
FIG. 3 is an elevational part sectional view showing the telescoping plunger being extended from the base.
Figure 4:
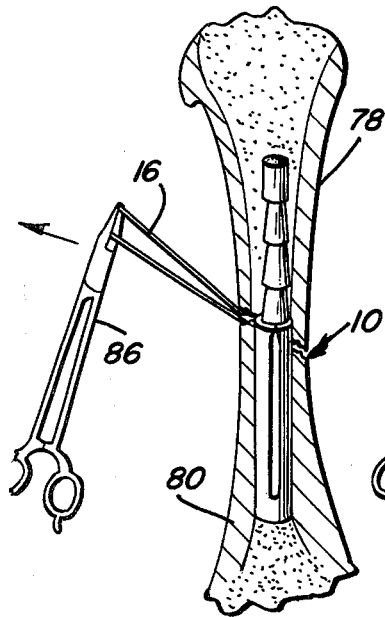
FIG. 4 is an elevational part sectional view showing the telescoping plunger extending into the second half of the fractured bone.

Now with reference to the figures, especially FIGS. 7 through 11, the intermedullary pin, generally designated by the numeral 10, of the present invention will be described. It will become immediately apparent, that the intermedullary pin has two main components, namely, base 12 and telescopingly plunger 14. The base and plunger may be constructed of any non-tissue responsive materials, such as Teflon, nylon, surgical stainless steel, etc. A third component of the device is the extension pull wire 16. This extension pull wire may be contructed of any suitable material, such as surgical stainless steel.

Base 12 consists of a pair of side walls 18 and 20 which are connected by an annular base bottom 22. The walls are separated by grooves 24 which are designed to be wide enough to accept wire 16. The free end of each wall terminates in a base retaining shoulder 25 which has radially converging walls forming widened abutment faces 26.

Plunger 14 has a longitudinally extending plunger head 28 and a series of frusto-conical sections 30 which form plunger retaining lips 32. The last frusto-conical section contains groove 34 therein for cooperation with wire 16. As will be readily apparent, the plunger retaining lips 32 coact with abutment faces 26 to provide one-way action for the plunger whereby walls 18 and 20 expand radially outward to allow removal of the plunger from the interior of the base. Abutment face 26 together with plunger retaining lips 32 provide an obstacle for the return of the plunger to the interior of the base.

As is also readily apparent, the extension pull wire 16 consists of one continuous length of wire formed in a loop. The loop of wire 16 is disposed in groove 34 of plunger 14 and extends out of side grooves 24 of base 12 for access thereto by the user.

FIGS. 12 and 14 demonstrate an alternative embodiment of the intermedullary pin wherein the cross section of the device is generally rectangular. Pin 36 of FIG. 12 operates in the same general way as the round pin described above. Pin 36 has a plunger 38, a base 40 and an extension pull wire 16'. The base of pin 36 contains a generally rectangular base bottom 42 which connects the side walls 44 and 46 which form grooves 48 therebetween. The free end of the walls 44 and 46 have retaining shoulders 50 which terminate in abutment faces 52 contained in the section of the wall which does not define side groove 48. In this manner, the wall will be allowed to flex outwardly in the direction of the portions containing the retaining shoulders and abutment faces.

Plunger 38 has a generally rectangular plunger head 54 followed by a series of truncated wedges 56 which contain plunger retaining lips 58 extending laterally of the plunger for coaction with abutment faces 52. It will be noted that the plunger contains two smooth sides which face the sides of the base containing slots 48.

Another embodiment of the invention may be seen with reference to FIGS. 13, 15 and 16 wherein a triangular version of the intermedullary pin is set forth. It will be readily apparent that the operation of the triangular embodiment of the intermedullary pin 60 is similar to that of those embodiments already described. The base 62 contains three walls 64 and three slots 66. The free ends of the walls terminate in retaining shoulder 68 with abutment faces 70. Triangular plunger 72 has plunger retaining lips 74 on three sides for interaction with the abutment faces 70. The bottom plunger has three notches 76, two of which may be used at a time for connection to wires 16". In this embodiment, it will be observed that the wire 16" will extend out of two of the three slots 66 provided for this purpose. In this manner, the wire may be oriented in a specific direction as desired by the user.

Figure 5:
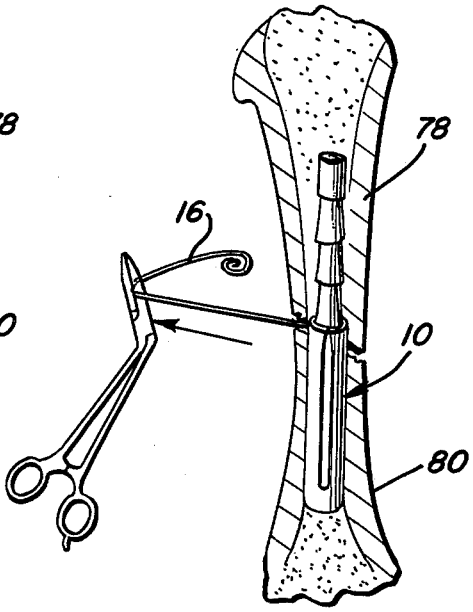
FIG. 5 is an elevational part sectional view showing the expansion device being removed from the bone.
Figure 6:
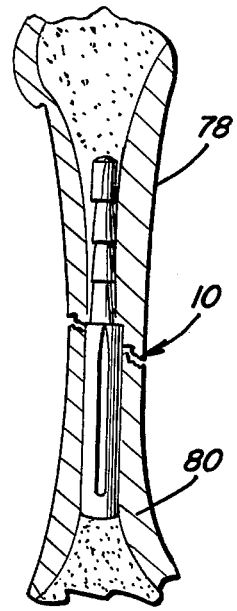
FIG. 6 is an elevational part sectional view showing the expanded plunger in its final position in the bone.

Now with references to FIGS. 1 through 6, the operation of the intermedullary pin will be described. First, the bone marrow cavity of each half of the bone 78 and 80 is drilled out to form cavities 82 and 84. The intermedullary pin is inserted completely into cavity 84 leaving extension pull string 16 extending from the cavity. The two halves of the bone 78 and 80 are then aligned with the pull string extending from the fracture therebetween. The pull string 16 is then firmly grasped by use of, for example, forceps 86. The pull string is moved laterally with respect to the bone which forces plunger 14 out of base 12 and into cavity 82. As shown in FIG. 5, when the plunger is extended to the desired length, string 16 is cut and removed entirely from the intermedullary pin. This then leaves the extended pin 10, as shown in FIG. 6, fully extended in the two cavities in the bone marrow.

As will be understood, the size and shape of the intermedullary pin may be varied in accordance with the size, length and position of the bone, together with the type of fracture contained therein. For example, it will be immediately apparent that the square and triangular embodiments of the present invention may positively prevent rotation of the plunger with respect to the base, while the round embodiment allows such rotation, thus indicating the use of one of these embodiments where rotation of the base halves may occur.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. An intermedullary pin device for use in setting bone fractures comprising: an elongated hollow tubular base portion for insertion into a drilled out cavity in one-half of a fractured bone; an elongated plunger portion adapted to be received in the hollow base to form a telescoping relationship therewith; extension means for connection to the plunger for extending the plunger from the base into a drilled out cavity in a second half of a fractured bone; and holding means for preventing the plunger from being reinserted into the base after it has been extended by the extension means.

2. The device of claim 1 wherein said holding means includes resilient means which flex to allow the plunger to extend from the base, and return to the unflexed position to prevent the plunger to return into the base.

3. The device of claim 2 wherein said holding means further includes a plurality of laterally extending projections spaced longitudinally along the plunger, said projections causing said resilient means to flex by an extension of the plunger and abut said resilient means to prevent reinsertion of the plunger into the base.

4. The device of claim 1 wherein said extension means includes a flexible loop connected to said plunger, said loop forming a slidable engagement with the plunger.

5. The device of claim 4 wherein said base contains at least one slit in the side thereof to allow the loop to engage the plunger toward the bottom of the plunger.

6. The device of claim 2 wherein the resilient means is formed by at least one longitudinally running slot in the base, said slot starting at the end of the base from which the plunger extends and allowing the sides of the base to flex outwardly.

7. An intermedullary pin device for use in setting bone fractures comprising: a base with a plunger telescopingly received therein, said base being adapted to be received within a drilled out cavity in one section of said fractured bone; a flexible extension means connected to said plunger for extending said plunger into a drilled out cavity in a second section of said fractured bone, said extension means being formed in a loop and being accessible externally of the bone.

8. The device of claim 7 wherein said extension means is slidably received in said plunger whereby the extension means may be removed from the plunger by cutting the loop and sliding the extension means out of engagement with the plunger.

9. The device of claim 8 and further including means attached to said plunger and said base to allow movement of said plunger in one direction only.

* * * * *